United States Patent [19]

Manschot

[11] Patent Number: 4,743,236
[45] Date of Patent: May 10, 1988

[54] COMBINATION URINE METER AND URINARY DRAINAGE BAG AND THE METHOD OF USE

[75] Inventor: James G. Manschot, Eagle, Wis.

[73] Assignee: Plastronics, Inc., Racine, Wis.

[21] Appl. No.: 910,878

[22] Filed: Sep. 24, 1986

Related U.S. Application Data

[63] Continuation-in-part of Ser. No. 735,399, May 17, 1985, abandoned.

[51] Int. Cl.⁴ .............................................. A61M 1/00
[52] U.S. Cl. .................................... 604/323; 128/762; 128/767
[58] Field of Search ............................... 604/323–327, 604/408, 410, DIG. 24, 335, 350; 383/9, 38, 44; 73/429, 426; 128/760, 761, 762, 766, 767, 771

[56] References Cited

U.S. PATENT DOCUMENTS 2,800,269 7/1957 Smith ......................... 128/DIG. 24
3,831,453 8/1974 McWhorter ........................ 604/323
3,865,165 2/1975 Glass .................................... 604/323
4,432,763 2/1984 Manschot et al. .......... 128/DIG. 24
4,503,864 3/1985 Powers ................................ 128/760
4,625,734 12/1986 Sherlock et al. ..................... 128/766

OTHER PUBLICATIONS

Cordis Advertising Sheet, Cordis External Ventricular Drainage Set, Cordis Corp., Miami, Fla. 33137, 1974.

Primary Examiner—C. Fred Rosenbaum
Assistant Examiner—J. L. Kruter
Attorney, Agent, or Firm—Fuller, Puerner & Hohenfeldt

[57] ABSTRACT

A urine collection device having a meter and collection chamber formed by a heat sealed portion which separates the two chambers. A passageway formed by the heat sealed portion and a sealed edge allows the collected urine to pass from one chamber to the other and dispensed from a discharge port when the urine collection device is hung selectively from either of two hangers located on the edges of the device.

9 Claims, 2 Drawing Sheets

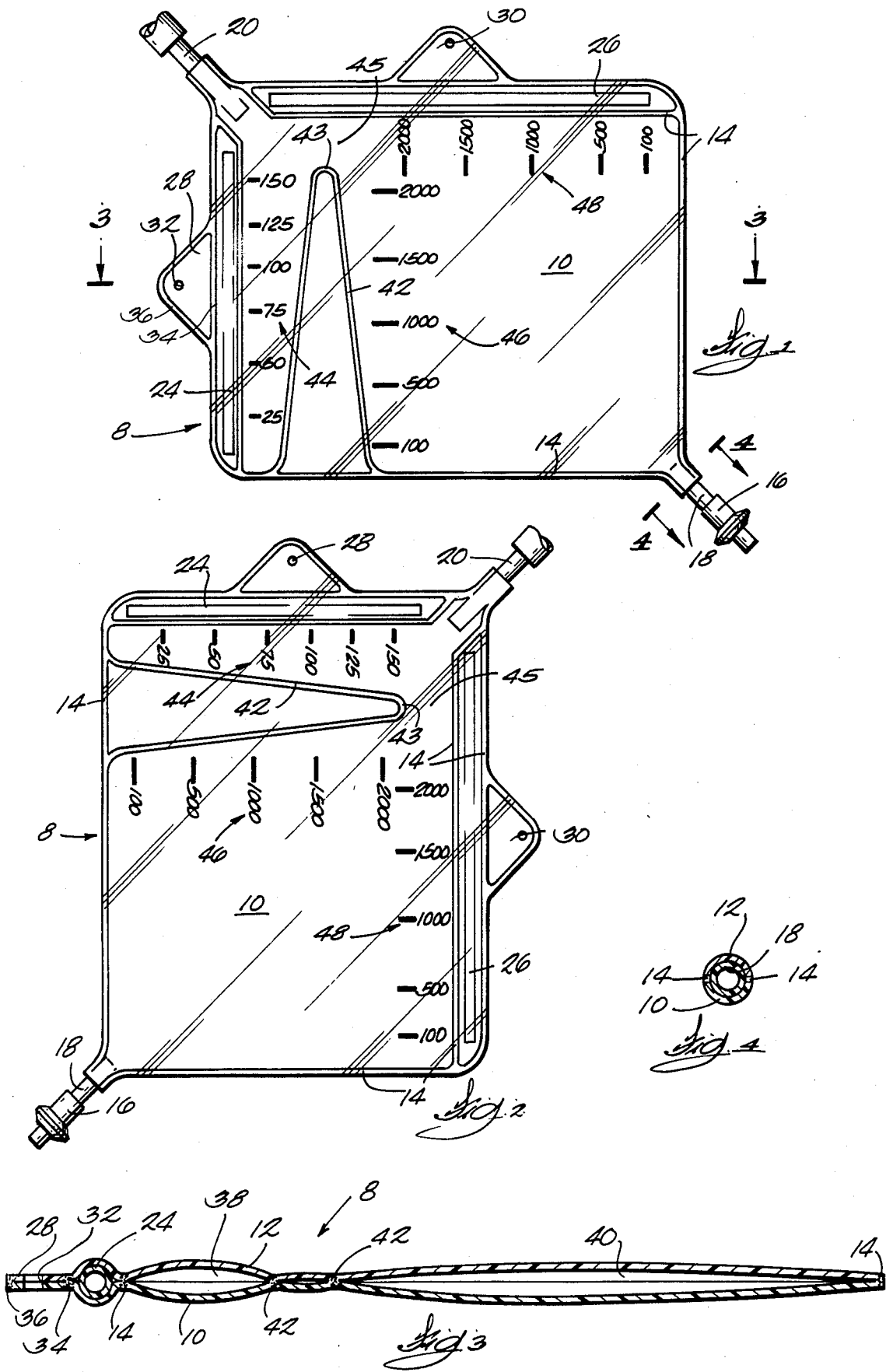

COMBINATION URINE METER AND URINARY DRAINAGE BAG AND THE METHOD OF USE

This application is a continuation-in-part application of application Ser. No. 735,399, filed May 17, 1985, now abandoned.

BACKGROUND OF THE INVENTION

1. Field of the Invention

This invention relates to a combination urine meter and urinary drainage bag.

2. Description of the Prior Art

Prior to this invention urine meters and urinary drainage bags were separate devices. An example of a urine meter is shown in U.S. Pat. No. Re. 30,607. An example of a urinary drainage bag shown in U.S. Pat. No. 4,363,406. The principal object of this invention is to provide a single unit which serves both as a urine meter and also as a urinary drainage bag. A further object of the present invention is to provide a unit which is of relatively simple construction and accordingly is relatively inexpensive to manufacture.

SUMMARY OF THE INVENTION

The invention in its simplest form is comprised of a sealed container having an inlet through which urine can flow into the interior of the container. A barrier means is provided for dividing the interior of the container into a urine metering compartment and a urine collection compartment. A hanger means is provided on the container for hanging the container in a meter operating position. A second hanger means is provided for hanging the container in a drainage operating position. A passageway means is provided which interconnects the urine metering compartment with the urine collection compartment. The inlet on the container is positioned so that urine flowing therethrough when the container is in its meter operating position will flow into and be collected in the urine metering compartment. The barrier means is constructed so that when the container is rotated from its metering operating position, urine will flow from the urine metering compartment through the passageway means and then into the urine collection compartment. When the unit is hung in its urine drainage position urine will flow directly from the inlet through the passageway and into the urine collection compartment.

DESCRIPTION OF THE INVENTION

FIG. 1 is a front elevation view of a preferred embodiment of the combination urine meter and urinary drainage bag of the present invention with the unit hanging in a first position for use as a urine meter;

FIG. 2 is a front elevation view similar to FIG. 1 but with the unit hanging in a second position for use as a urinary drainage bag;

FIG. 3 is an enlarged fragmentary sectional view taken along line 3—3 of FIG. 1; and FIG. 4 is an enlarged sectional view taken along line 4—4 of FIG. 1;

DESCRIPTION OF THE PREFERRED EMBODIMENT

Figure 5:
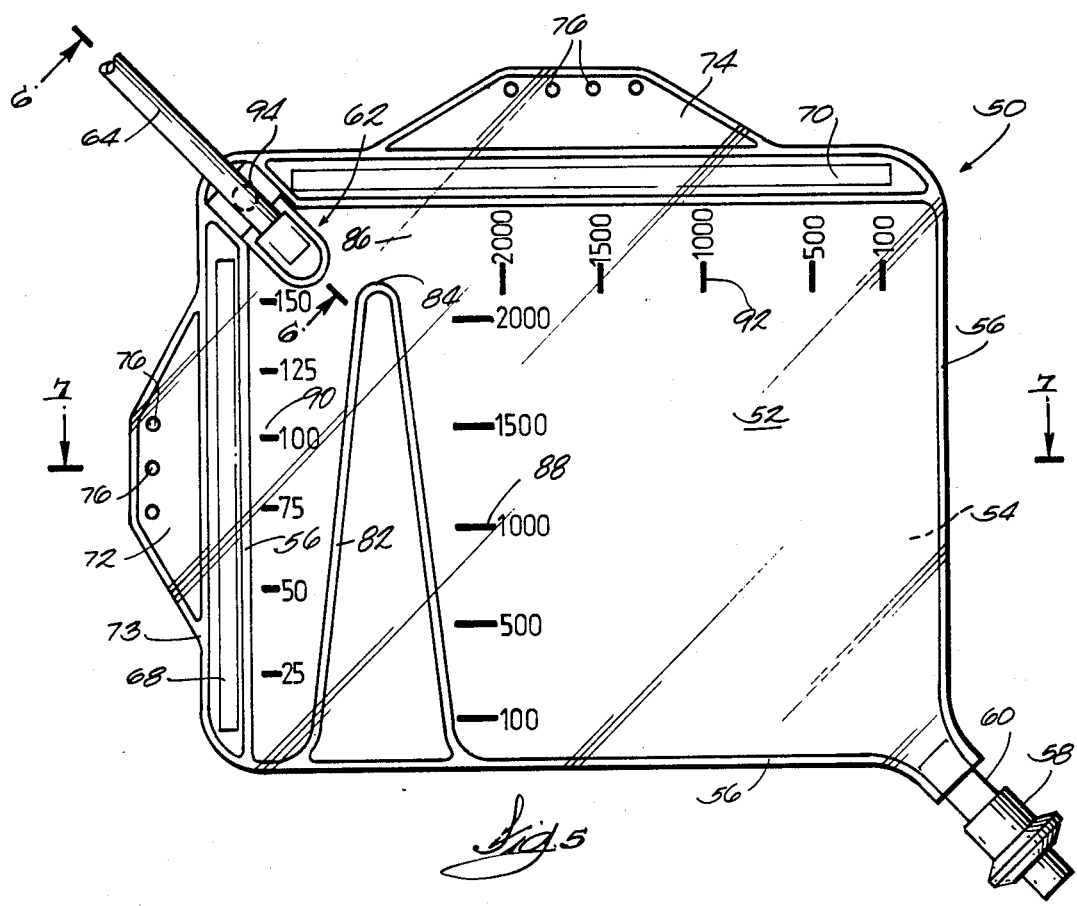
FIG. 5 is a front elevation view of a second embodiment of the combination urine meter and urinary drainage bag of the present invention with the unit hanging in a first position for use as a urine meter.

Referring to FIGS. 1 and 3, in the preferred embodiment of the present invention the combination urine meter and urinary drainage bag 8 is comprised of a front sheet 10 and a back sheet 12 of fluid impervious flexible material such as polyvinyl cloride. The front sheet 10 and back sheet 12 are sealed along their marginal edge 14 to form a sealed flexible bag container.

The unit 8 is provided with a drainage valve 16 in the lower right-hand corner thereof (as viewed in FIG. 1) mounted on a tube 18 inserted and sealed between front and back sheets 10 and 12 as shown in FIG. 4.

The urine meter 8 is provided with an inlet assembly 22 of any suitable design through which fluid from tube 20 flows into the unit 8. Inlet assembly 22 is located at the upper left-hand portion of the meter as viewed in FIG. 1.

The unit is provided with a pair of stabilizer bars 24, 26 mounted along the vertical and horizontal edges of the unit as viewed in FIG. 1. Bar 24 is captured between front and back sheets 10 and 12 as shown in FIG. 3. Bar 26 is also captured between sheets 10 and 12 along the top edge of the unit in a manner like that shown in FIG. 3.

The unit 8 is provided with a pair of hanging tabs 28 and 30 located on the left-hand and top edges of the unit as shown in FIG. 1. Hanging tabs 28 and 30 have openings 32 therein for purposes of connecting the tabs to a hanging hook or other similar part. As shown in FIG. 3 seal lines 34 and 14 serve to capture bar 24 and also serve to form the outer edge of hinge tab 28. The construction of the top hanging tab 30 is the same as tab 28.

The sealed internal portion of the unit 8 is divided into two compartments 38 and 40 by a seal line 42 as best shown in FIG. 3. The smaller compartment 38 serves as a metering compartment and the larger compartment 40 serves as a collection compartment as will be described in detail hereinafter.

In the preferred embodiment seal line 42 as well as seal lines 14, 34 and 36 are made by an electronic welding process.

As best shown in FIG. 1, seal line 42 extends from the left end of seal line 14 at the bottom of the unit and then angles upwardly therefrom to a point 43 spaced a short distance from seal line 14 at the top edge of the unit. The seal line 42 makes a gentle curve at point 43 and then angles downwardly to seal line 14 at the bottom edge of the unit. The gentle curve at point 43 prevents the creation of a stress point in this area.

Thus it is seen that with the unit in the FIG. 1 position, seal line 42 serves as a barrier between compartments 38 and 40 leaving a relatively small interconnecting passageway 45 between the compartments which passageway is defined by the space between point 43 and the seal line 14 along the top of the unit.

The front sheet 10 of the unit is provided with volumetric scales 45, 46 and 48 the function of which will be explained hereinafter.

Figure 6:
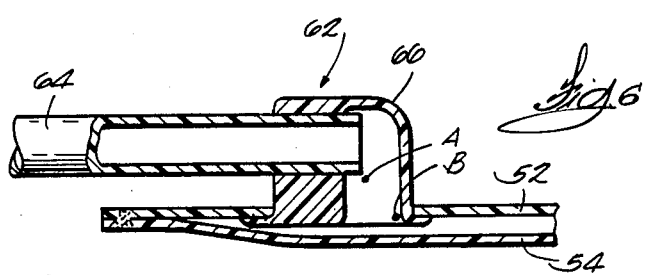
FIG. 6 is a sectional view taken along line 6—6 of FIG. 5.

Referring to FIGS. 5 and 6, in the second embodiment of the present invention the combination urine meter and urinary drainage bag 50 is comprised of a front sheet 52 and a back sheet 54 of fluid impervious flexible material such as polyvinyl cloride. The front sheet 52 and the back sheet 54 are sealed along their marginal edge 56 to form a sealed flexible bag container.

The unit 50 is provided with a drainage valve 58 in the lower right-hand corner thereof (as viewed in FIG. 5) mounted on a tube 60 inserted and sealed between front and back sheets 52 and 54.

The urine meter 50 is provided with an inlet drip tube assembly 62 through which fluid from tube 64 flows into the unit 50. Inlet assembly 62 is located at the upper left-hand portion of the meter as viewed in FIG. 5. Tube 64 enters the meter at an angle of about 45 degrees with respect to the horizontal. As shown in FIG. 6, tube 64 is inserted in a drip tube housing 66 with the end of the tube spaced from the housing walls. The distance between the drip site (A) on the tube 64 and the point (B) at which drops hit the inlet surface must be great enought to prevent bridging of the liquid between the two points. Such distance shall be at least 3 mm.

Figure 7:
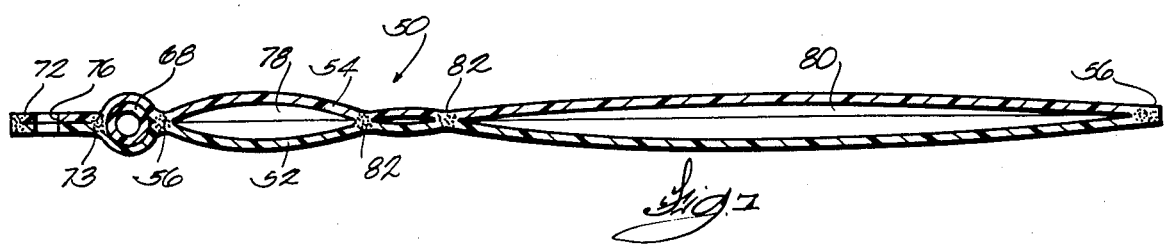
FIG. 7 is a sectional view taken along line 7—7 of FIG. 5.

The unit is provided with a pair of stabilizer bars 68, 70 mounted along the vertical and horizontal edges of the unit as viewed in FIG. 5. Bar 68 is captured between front and back sheets 52 and 54 as shown in FIG. 7. Bar 70 is also captured between sheets 52 and 54 along the top edge of the unit in a manner like that shown in FIG. 7. Bars 68 and 70 serve two functions i.e. to insure that the unit hangs properly in both hanging positions and to facilitate accurate reading of the volumetric scales.

The unit 50 is provided with a pair of hanging tabs 72 and 74 located on the left-hand and top edges of the unit as shown in FIG. 5. Hanging tabs 72 and 74 have openings 76 therein for purposes of connecting the tabs to a hanging hook or other similar part. As shown in FIG. 7, seal lines 73 and 56 serve to capture bar 68. The construction of the top hanging tab 74 is the same as tab 72.

As shown in FIG. 7, the sealed internal portion of the unit 50 is divided into two compartments 78 and 80 by a seal line 82. The smaller compartment 78 serves as a metering compartment and the larger compartment 80 serves as a collection compartment.

As best shown in FIG. 5, seal line 82 extends from the left end of seal line 56 at the bottom of the unit and then angles upwardly therefrom to a point 84 spaced a short distance from seal line 56 at the top edge of the unit. The seal line 82 makes a gentle curve at point 84 and then angles downwardly to seal line 56 at the bottom edge of the unit. The gentle curve at point 84 prevents the creation of a stress point in this area.

Thus it is seen that with the unit in the FIG. 5 position, seal line 82 serves as a barrier between compartments 78 and 80 leaving a relatively small interconnecting passageway 86 between the compartments which passageway is defined by the space between point 84 and the seal line 56 along the top of the unit.

The front sheet 10 of the unit is provided with volumetric scales 88, 90 and 92 the function of which will be explained hereinafter. A vent assembly 94 is mounted on the upper portion of front sheet 52. Vent assembly 94 is mounted in the upper left hand corner above drip tube inlet assembly 62 so that incoming liquid will not flow past the vent assembly in either of the two hanging positions of unit 50.

OPERATION

In normal use as a urine meter the unit is hung in the FIG. 1 position by means of hanging tab 30. In such position urine from the patient flowing through tube 22 into the unit will collect in compartment 38 to the left of seal line 42.

The rate of flow can be determined by monitoring the flow using scale 44 relative to a predetermined period of time. When it is desired to obtain a subsequent reading the urine which has collected in compartment 38 can be emptied into collection compartment 40 by simply rotating it approximately 90 degrees to a position substantially like that shown in FIG. 2. In such position urine will flow from compartment 38 to compartment 40 through the passageway 45 defined by the space between the seal line point 43 and the seal line 14 along the top of the unit. After compartment 38 has been emptied the unit is returned to its original FIG. 1 hanging position and a second flow rate can be determined. Scale 46 indicates the volume of urine which collects in compartment 40. Compartment 40 can be drained by means of valve 16.

After a period wherein the rate of urine flow from a patient is monitored by the procedure described above, such monitoring is often no longer necessary. At such time, however, it is often necessary to simply collect urine flowing from the patient. In such an event the conventional practice is to replace the urine metering device with a urinary drainage bag in which event the urine meter is disposed of. Such sequential treatment of the patient thus required two separate devices namely a urine meter and a urinary drainage bag.

The unit 8 described herein is designed not only to function as a urine meter as described above, but in addition the unit 8 is capable of also functioning as a urinary drainage bag. Thus, for example, when the metering function is no longer required the unit 8 can be converted to a drainage bag by simply repositioning the unit from its FIG. 1 hanging position to the hanging position shown in FIG. 2. In such FIG. 2 position hanging tab 28 is put into use.

In the FIG. 2 position urine flowing from the patient through tube 22 will enter the unit in the upper right hand corner thereof. Such flow will pass directly through the passageway 45 and be collected in the bottom of large collection compartment 40. Scale 48 serves to indicate the volume of urine collected in compartment 40 when the unit is used as a urinary drainage bag.

The operation of the embodiment shown in FIGS. 5, 6 and 7 is the same as that described above for the embodiment shown in FIGS. 1, 2, 3 and 4.

I claim:
1. A combination urine meter and urinary drainage bag comprising:
   a sealed container having an inlet means through which urine can flow into the interior of said container, said sealed container including a front and back sheet of fluid impervious flexible material sealed along the edges thereof, said sealed container having a top edge, a bottom edge and two side edges;
   a drainage tube in fluid communication with said inlet means,
   a first hanger means mounted on the top edge of said container for hanging said container in a meter operating position;
   stiffener means comprising a first stiffener member mounted along the top edge of said container and a second stiffener member mounted along said side edge of said container, said inlet means located in a corner of said sealed container between the ends of said first and second stiffener members;
   a barrier means for dividing the interior of the container into a urine metering compartment and a urine collection compartment, said barrier means comprised of a seal line between said front and back sheets which extends from the bottom edge of said sealed container at an angle to a point spaced from the top edge of said container and then curves downwardly at an angle to said bottom edge of said container;

said inlet means on said container positioned so that urine flowing therethrough when said container is in its meter operating position will flow into and be collected in said urine metering compartment;

passageway means interconnecting said urine metering compartment with said urine collection compartment, said passageway means defined by the space between the top portion of said seal line and the top edge of said sealed container;

said passageway means serving to allow flow of urine from said metering compartment to said urine collection compartment when the meter is rotated from its meter operating position, said passageway means further serving to allow flow of urine from said inlet into said urine collection compartment when said meter is in its urine drainage operating position; and a drainage outlet means located in the lower portion of said urine collection compartment; and a second hanger means mounted on a side edge of said container for hanging said container in a urinary drainage operating position wherein urine will flow directly from said inlet means into said urine collection compartment when said container is in said urinary drainage operating position.

2. A combination urine meter and urinary drainage bag comprising:

a sealed container having an inlet means through which urine can flow into the interior of said container, said sealed container including a front and back sheet of fluid impervious flexible material sealed along the edges thereof, and sealed container having a top edge, a bottom edge and two side edges, said inlet means including a drip chamber assembly comprised of an inlet tube mounted in a drip tube housing with the end of said inlet tube spaced a sufficient distance from the inlet surface to prevent bridging of liquid between the tube and the surface;

a first hanger means mounted on the top edge of said container for hanging said container in a meter operating position;

a second hanger means mounted on a side edge of said container for hanging said container in a urinary drainage operating position;

stiffener means comprising a first stiffener member mounted along the top edge of said container and a second stiffener member mounted along said side edge of said container of which said second hanger means is mounted, said inlet means located in a corner of said sealed container between the ends of said first and second stiffener members;

a barrier means for dividing the interior of the container into a urine metering compartment and a urine collection compartment, said barrier means comprised of a seal line between said front and back sheets which extends from the bottom edge of said sealed container at an angle to a point spaced from the top edge of said container and then curves downwardly at an angle to said bottom edge of said container;

said inlet on said container positioned so that urine flowing therethrough when said container is in its meter operating position will flow into and be collected in said urine metering compartment;

passageway means interconnecting said urine metering compartment with said urine collection compartment, said passageway means defined by the space between the top portion of said seal line and the top edge of said sealed container;

said passageway means serving to allow flow of urine from said metering compartment to said urine collection compartment when the meter is rotated from its meter operating position, said passageway means further serving to allow flow of urine from said inlet into said urine collection compartment when said meter is in its urine drainage operating position; and a drainage outlet means located in the lower portion of said urine collection compartment.

3. A combination urine meter and urinary drainage bag according to claim 2 in which the bridging distance between the end of the tube and the inlet surface is at least 3 mm.

4. A combination urine meter and urinary drainage bag comprising:

a sealed container having an inlet means through which urine can flow into the interior of said container, said sealed container including a front and back sheet of fluid impervious flexible material sealed along the edges thereof, said sealed container having a top edge, a bottom edge and two side edges;

a first hanger means mounted on the top edge of said container for hanging said container in a meter operating position;

a barrier means for dividing the interior of the container into a urine metering compartment and a urine collection compartment, said barrier means comprised of a seal line between said front and back sheets which extends from the bottom edge of said sealed container at an angle to a point spaced from the top edge of said container and then curves downwardly at an angle to said bottom edge of said container;

said inlet means on said container positioned so that urine flowing therethrough when said container is in its meter operating position will flow into and be collected in said urine metering compartment;

a drainage tube in fluid communication with said inlet means;

passageway means interconnecting said urine metering compartment with said urine collection compartment, said passageway means defined by the space between the top portion of said seal line and the top edge of said sealed container;

said passageway means serving to allow flow of urine from said metering compartment to said urine collection compartment when the meter is rotated from its meter operating position; and a second hanger means mounted on a side edge of said container for hanging said container in a urinary drainage operating position wherein urine will flow directly from said inlet means into said urine collection compartment when said container is in said urinary drainage operating position.

5. A combination urine meter and urinary drainage bag according to claim 4 in which the portion of said front sheet opposite said urine metering compartment has a vertically extending volumetric scale thereon when the unit is viewed in its first hanging position.

6. A combination urine meter and urinary drainage bag according to claim 5 in which the portion of said front sheet opposite said urine collection compartment has a vertically extending volumetric scale thereon when the unit is viewed in its first hanging position.

7. A combination urine meter and urinary drainage bag according to claim 6 in which the portion of said front sheet opposite said urine collection compartment has a vertically extending volumetric scale thereon when the meter is viewed in its second hanging position.

8. The method of collecting urine from a patient comprising the step of:
   (a) providing a urine collection device, said device having an inlet in fluid communication with a patient, and having a hangar means on two contiguous edge portions providing two hanging positions;
   (b) receiving a flow of urine from a patient into a metering chamber of a urine collection device when the device is in a first hanger position, said chamber having a volumetric scale thereon to facilitate volumetric determination of flow into said chamber;
   (c) periodically emptying said metering chamber by rotating the device approximately 90 degrees to thus cause flow from said metering chamber into a collection chamber in said device; and
   (d) moving said device from the first hanging position to a second hanging position wherein flow of urine from the patient will flow directly into said collection chamber to thus convert said device from a urine metering function to a urine collection function.

9. The method of collecting urine from a patient according to claim 8 in which said first hanging position of said device is approximately 90 degrees from said second hanging position of said device.

* * * * *

UNITED STATES PATENT AND TRADEMARK OFFICE
CERTIFICATE OF CORRECTION

PATENT NO. : 4,743,236
DATED : May 10, 1988
INVENTOR(S) : JAMES G. MANSCHOT

It is certified that error appears in the above—identified patent and that said Letters Patent is hereby corrected as shown below:

Column 7, Line 17    Delete "hangar" and substitute therefor --- hanger ---

Column 8, Line 1     Delete "hanger" and substitute therefor --- hanging ---

Signed and Sealed this

Twenty-fifth Day of October, 1988

*Attest:*

DONALD J. QUIGG

*Attesting Officer*    Commissioner of Patents and Trademarks